United States Patent [19]
Valducci

[11] Patent Number: 5,871,775
[45] Date of Patent: Feb. 16, 1999

[54] CONTROLLED RELEASE PHARMACEUTICAL COMPOSITIONS FOR THE ORAL ADMINISTRATION CONTAINING NIFEDIPINE AS ACTIVE SUBSTANCE

[75] Inventor: Roberto Valducci, Savignano Sul Rubicone, Italy

[73] Assignee: Valpharma S.A., Serravalle, San Marino

[21] Appl. No.: 925,966

[22] Filed: Sep. 9, 1997

[30] Foreign Application Priority Data

Sep. 27, 1996 [IT] Italy .............................. MI96A1983 U

[51] Int. Cl.⁶ ..................................................... A61K 9/48
[52] U.S. Cl. ......................... 424/451; 424/464; 424/486; 424/487; 514/772.5; 427/2.15
[58] Field of Search ................................ 424/502, 451, 424/464, 486, 487; 514/772.5; 427/2.15

[56] References Cited

U.S. PATENT DOCUMENTS

| | | |
|---|---|---|
| 4,606,911 | 8/1986 | Hayashi et al. . |
| 5,145,683 | 9/1992 | Rhodes . |
| 5,209,933 | 5/1993 | MacFarlane et al. . |

FOREIGN PATENT DOCUMENTS

| | | |
|---|---|---|
| 1184118 | 3/1985 | Canada . |
| 0220760 | 8/1981 | European Pat. Off. . |
| 0143857 | 11/1983 | European Pat. Off. . |
| 0047899 | 1/1984 | European Pat. Off. . |
| 0143857 | 6/1985 | European Pat. Off. . |
| 0315960 | 11/1988 | European Pat. Off. . |
| 0 220 760 | 8/1991 | European Pat. Off. . |
| 0220760 | 8/1991 | European Pat. Off. . |
| 0315960 | 8/1991 | European Pat. Off. . |
| 0740934 | 11/1996 | European Pat. Off. . |
| 2166651 | 5/1986 | United Kingdom . |
| 93/13773 | 7/1993 | WIPO . |
| 9313773 | 7/1993 | WIPO . |
| 9636318 | 11/1996 | WIPO . |

OTHER PUBLICATIONS

European Search Report, Mar. 24, 1997, Examiner Ventrua Amat, A.

Primary Examiner—Thurman K. Page
Assistant Examiner—Brian K. Seidleck

[57] ABSTRACT

Controlled release pharmaceutical compositions for the oral administration of nifedipine are disclosed which comprise an amorphous coprecipitate of nifedipine and polyvinylpyrrolidone with suitable excipients. The release rate may be varied from 8 to 24 hours by varying the amounts of the cellulose derivative, the carboxypolymethylene and the lactose.

13 Claims, 4 Drawing Sheets

CONTROLLED RELEASE PHARMACEUTICAL COMPOSITIONS FOR THE ORAL ADMINISTRATION CONTAINING NIFEDIPINE AS ACTIVE SUBSTANCE

PRIOR ART

The nifedipine represents the most studied and used inhibitor of the passage of the calcium ions in the slow flowing channels which affect the myocardium, the vasal smooth musculature and the sinoatrial (SA) and atrioventricular (AV) nodes.

The administration of nifedipine determines an increase of the coronary flow and a reduction of the peripheral vascular resistances while it has not practical interference with the SA and AV nodes. Consequently the nifedipine has been used for years for the hypertensive forms therapy and for the anginal syndrome control in often multifactorial therapeutical protocols and for treatments protracted in time, as a result of the chronic proceeding of such pathologies.

The nifedipine is a crystalline powder, insoluble in water, soluble in acetone and in other organic solvents, sensitive to light of different wavelengths, including the ultraviolet one.

The absorption of the nifedipine presents a strong inter-individual variability and, as it is a matter of the reference drug of an important therapeutical category, several studies have been directed to verify possible correlations among the physical characteristics, the pharmaceutical forms and the therapeutic efficacy.

The poor solubility in water of nifedipine in crystals causes in fact a low bioavailability.

For the above reported problems various solutions have been proposed which, however, show the drawback to give unsatisfactory results or they result being excessively complex.

The importance of the crystals size, for therapeutic efficacy purposes, is proved in the Patent EP 0047899, wherein the formulations obtained from very fine nifedipine crystals, having a specific surface ranging from 0.5 to 6 $m^2/g$, are proposed.

In the Patent EP 0220760B1, the nifedipine bioavailability is correlated to the micronization processes of the active principle in order to obtain "an extremely high specific surface".

Even technically complex solutions such as the nifedipine dissolution in derivatives of the tetrahydrofurfuryl alcohol and the subsequent dosage in capsules of soft gelatin have been adopted (Patent EP 0143857) in order to overcome the variables linked to the crystals size.

The Patent EP 0315960 proposes aqueous or hydro-alcoholic solutions in order to increase the bioavailability: certainly the variability linked to the crystals is overcome but problems such as a lower stability and a greater productive complexity are introduced.

The Patent WO 93/13773 describes controlled release formulations obtained from a mixture of 3 components (nifedipine, polyvinylpyrrolidone or derivatives, and acrylic based polymers) which, deposited on particles of a hydro-soluble carrier, allows to obtain formulations suitable for a single daily administration.

The Patent GB 2166651A concerns the production of controlled release microparticles from 0.1 to 125 micrometers, named "pharmasomes", obtained by a complex technique wherein the drug (nifedipine in the Example no. 3) and suitable polymers are solubilized and then emulsionated. The solvent phase is subsequently removed in order to obtain a powder coated to mask the flavour or to obtain the controlled release.

SUMMARY

The problems of the prior art are overcome by the controlled release pharmaceutical compositions for the oral administration containing nifedipine as active substance according to the present invention.

Said compositions comprise:
  an amorphous coprecipitate of nifedipine and polyvinylpyrrolidone;
  a hydrophile derivative of cellulose in an amount by weight ranging from 0.1 to 6 times with respect to the nifedipine;
  carboxypolymethylene and lactose in an amount by weight ranging from 0.1 to 5 times with respect to the nifedipine and
  a protective or retarding superficial coating.

Said compositions may be prepared in tablets or capsules shape having a release time ranging from 8 to 24 hours.

DETAILED DESCRIPTION OF THE INVENTION

The preparation of the controlled release pharmaceutical compositions for the oral administration containing nifedipine as active substance according to the present invention first of all provides for the preparation of an amorphous coprecipitate of nifedipine and polyvinylpyrrolidone and subsequently the use of said coprecipitate for the preparation of compositions in mixture with suitable excipients.

The coprecipitate of nifedipine and polyvinylpyrrolidone is prepared by the following process.

A solution of nifedipine and polyvinylpyrrolidone is prepared in an organic solvent, preferably methylene chloride, having a concentration of nifedipine ranging from 2.5 to 20% by weight and a ratio by weight between nifedipine and polyvinylpyrrolidone ranging from 1:1 to 1:5. Then the obtained solution is treated in a spray-drier plant at a temperature equal to 90° C.

The obtained coprecipitate has the shape of an amorphous powder and, analyzed by differential scanning calorimetry (DSC) is endothermic melting peak at about 175° C. free, characteristic of the nifedipine crystals.

Figure 1:
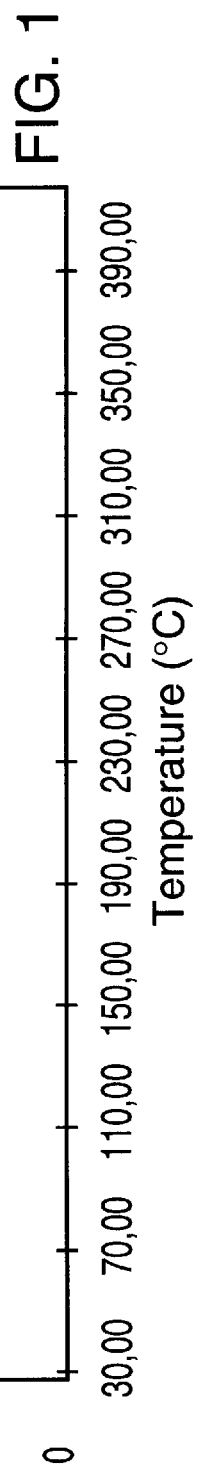
FIG. 1 represents the differential scanning calorimetric (DSC) diagram of the coprecipitate of nifedipine and polyvinylpyrrolidone of Example 1.

In FIG. 1 the diagram obtained with the coprecipitate obtained in the Example 1 described below is reported and, for comparison, in FIG. 2 the characteristic diagram of the nifedipine crystals is reported. The coprecipitate amorphous character is confirmed by the X-ray crystallogram of FIG. 4 relative to the coprecipitate of nifedipine and polyvinylpyrrolidone in comparison with the crystallogram of FIG. 3 relative to the nifedipine.

The coprecipitate used in the preparation of the compositions according to the present invention has a granulometry lower than 100 micrometers.

The preparation of the compositions in tablets shape is realized according to the following process.

A granulate is prepared by the fluidized bed technique introducing the coprecipitate of nifedipine and polyvinylpyrrolidone, a hydrophile derivative of cellulose in an amount by weight ranging from 0.1 to 6 times by weight with respect to the nifedipine and carboxypolymethylene and lactose in an amount by weight ranging from 0.1 to 5 times with respect to the nifedipine. Moreover substances as talc, magnesium stearate and colloidal silica, suitable to aid the technological process are added.

Purified water is used for the granulation. Then the obtained granules are transformed in tablets which are coated with a protective or retarding superficial film.

Said hydrophile derivative of cellulose is selected from the group consisting of hydroxypropylmethylcellulose, hydroxyethylcellulose, hydroxymethylcellulose, hydroxypropylcellulose, carboxymethylcellulose, or mixtures of the same and other derivatives of the cellulose.

The retarding superficial coating contains a material selected from the group consisting of an acrylic polymer, an alkylcellulose, paraffin, stearic acid, shellac, hydrogenated vegetable oil or a mixture in any proportion of the previous and possible plasticizers such as for example diethylphthalate, dibutylphthalate, glyceryl triacetate, polyethylene glycols.

The preparation of the capsule-shaped compositions may be realized using the same granules used for the tablets, or it may be realized applying the coprecipitate of nifedipine and polyvinylpyrrolidone on saccharose and starch inert cores which are subsequently coated with said retarding material in order to obtain spheroidal particles having a diameter ranging from 700 to 1400 micrometers, using for example the fluidized bed technique.

As it is observed in the description of the prior art, the nifedipine is used in therapy for the treatment of diseases such as the essential hypertension and the angina cordis, with protocols necessarily protracted in time and frequently in association with other drugs.

The compositions according to the present invention are able to help the posological scheme for the patient allowing one or two administrations a day.

In fact the release of the nifedipine from said compositions is modulable from 8 to 24 hours by varying the amounts of the hydrophile derivative of cellulose, of the carboxypolymethylene and of the lactose as shown by the examples.

In addition to the tablets and capsules shape, said compositions may also be prepared in other forms such as for example pills, confections, single dose or multi-dose granules with dispenser, spheroids, etc.

The nifedipine content for dosage unit is ranging from 0.1 to 400 mg. Moreover, the compositions according to the present invention have the advantage to be prepared by a simpler and cheaper process with respect to the prior art one.

Operating according to the known technique, for example according to the GITS (gastrointestinal therapeutic system) technology only with very sophisticated processes it is possible to obtain compositions having characteristics similar to the compositions according to the present invention ones. The GITS technique is described in "Nifedipine Gastrointestinal Therapeutic System" (Dec. 21, 1987. The American Journal of Medicine, Vol. 83 Suppl. 6B).

For illustrative aim of the invention the following Examples are reported.

EXAMPLE 1

Preparation of the coprecipitate of nifedipine and polyvinylpyrrolidone.

1.0 Kg of nifedipine and 1.0 Kg of polyvinylpyrrolidone are dissolved in 18 liters of methylene chloride at room temperature.

The obtained solution is treated in a spray-drier plant at a temperature equal to 90° C. with double fluid nozzle with external mixing.

A solid coprecipitate having a ratio by weight between nifedipine and polyvinylpyrrolidone equal to 1:1 and a granulometry lower than 100 micrometers is obtained.

Figure 2:
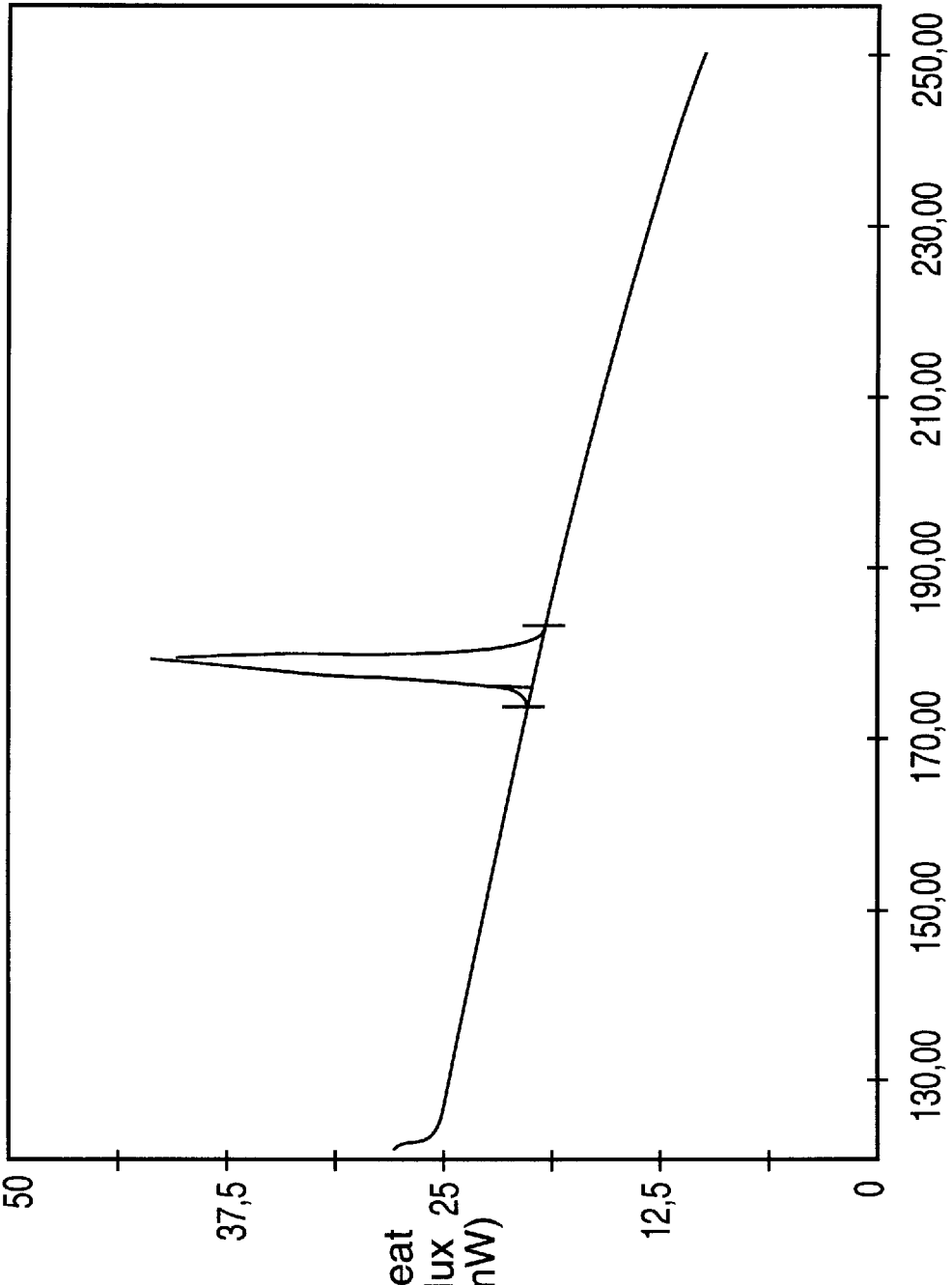
FIG. 2 represents the differential scanning calorimetric (DSC) diagram of nifedipine crystals.

This coprecipitate, analyzed by differential scanning calorimetry gives a diagram (FIG. 1) endothermic melting peak at about 175° C. free characteristic of the nifedipine crystals (FIG. 2, reported as comparison).

Figure 3:
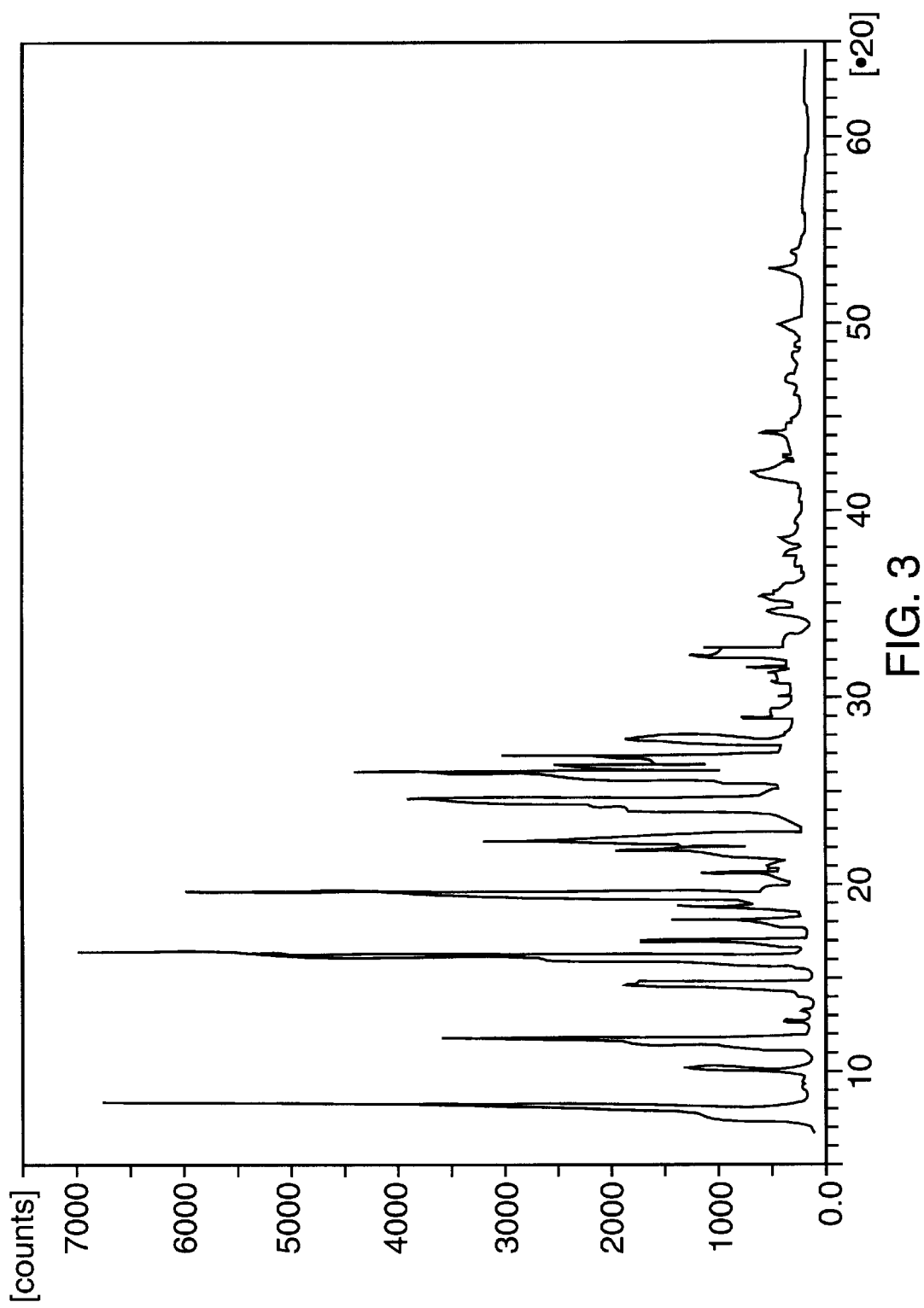
FIG. 3 represents the X-ray crystallogram of nifedipine.
Figure 4:
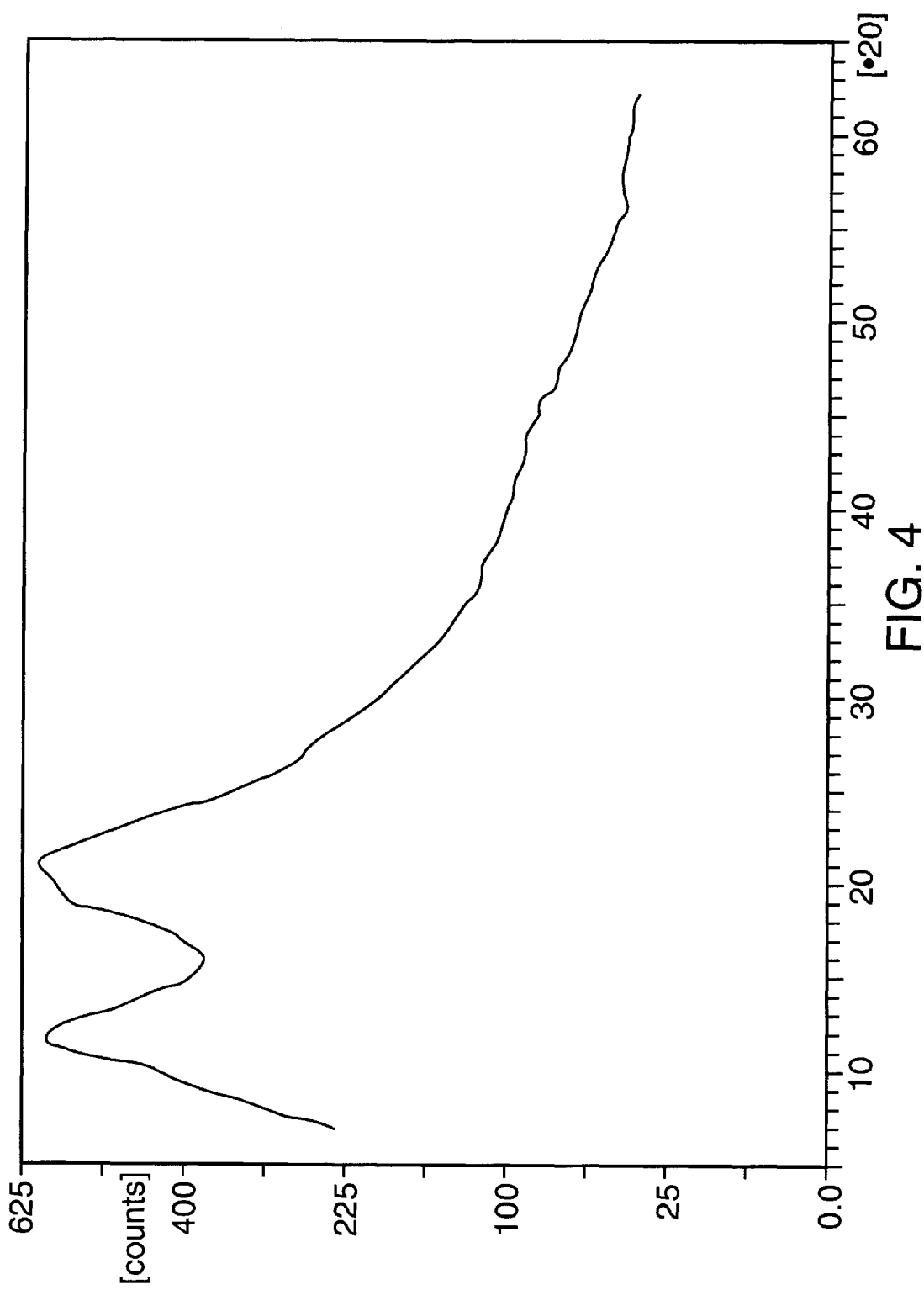
FIG. 4 represents the X-ray crystallogram of the coprecipitate of nifedipine and polyvinylpyrrolidone of Example 1.

Moreover the amorphous character of the coprecipitate is confirmed by the comparison of the X-ray crystallogram of the FIG. 4 (coprecipitate) with the crystallogram of the FIG. 3 (nifedipine).

EXAMPLE 2

Composition in tablets of 30 mg of nifedipine.

A tablet composition is prepared using the coprecipitate of nifedipine and polyvinylpyrrolidone 1:1, obtained as previously described, having a granulometry lower than 100 micrometers.

A granulate is first prepared introducing in a fluid bed plant hydroxypropylmethylcellulose, carboxypolymethylene and talc, in addition to the coprecipitate of nifedipine and polyvinylpyrrolidone. Purified water is used in order to obtain the granules which, mixed with magnesium stearate and colloidal silica, allow to obtain some tablets which are subsequently coated with an opaque, protective film. In the following Table the percent composition relative either to the substances of the tablet or to the substances of the coating is reported.

Substances of the tablet nifedipine 15.96% by weight
polyvinylpyrrolidone 15.96% by weight
talc 30.31% by weight
hydroxypropylmethylcellulose 31.91% by weight
carboxypolymethylene 1.60% by weight
magnesium stearate 1.06% by weight
colloidal silica 1.60% by weight
Substances of the coating
talc 0.49% by weight
magnesium stearate 0.24% by weight
titanium dioxide 0.37% by weight
iron oxide 0.04% by weight
acrylic acid copolymer 0.37% by weight
polyethylene glycol 4000 0.08% by weight
The tablets had an average weight equal to 188 mg and they have been analyzed according to the dissolution method using the test 2 described in the USP (Paddle<711>Dissolution).

The obtained results are shown in Table 1.

TABLE 1

| Hours | Example 2 Dissolution % |
|---|---|
| 1 | 10.3 |
| 4 | 52.0 |
| 8 | 95.2 |

EXAMPLE 3

Compositions in tablets of 60 mg of nifedipine.

Using the granulate described in the Example 2 tablets having an average weight equal to 376 mg have been prepared and they have been submitted to the dissolution test as in the Example 1. The obtained results are reported in Table 2

TABLE 2

| Hours | Example 3 Dissolution % |
|---|---|
| 1 | 11.9 |
| 4 | 49.8 |
| 8 | 83.5 |
| 12 | 97.5 |

EXAMPLE 4

Compositions in tablets suitable for a single daily administration equivalent to 30 mg of nifedipine.

With a process analogous to the one described in the Example 2 a granulate has been prepared which mixed with compression excipients has been transformed in tablets containing 30 mg of nifedipine. The tablets have been subsequently coated with an opaque film.

Substances of the tablet nifedipine 17.96% by weight polyvinylpyrrolidone 17.96% by weight talc 35.93% by weight hydroxypropylmethylcellulose 7.19% by weight carboxypolymethylene 7.19% by weight magnesium stearate 1.20% by weight colloidal siliceous earth 1.80% by weight lactose 8.98% by weight Substances of the coating acrylic acid copolymer 0.42% by weight talc 0.55% by weight magnesium stearate 0.28% by weight titanium dioxide 0.41% by weight iron oxide 0.04% by weight polyethylene glycol 4000 0.09% by weight The obtained results are reported in Table 3 and compared with the commercial product obtained from the equivalent dosage GITS technology.

TABLE 3

| Hours | Example 4 Dissolution % | 30 mg GITS tablets Dissolution % |
|---|---|---|
| 1 | 2.6 | 3.0 |
| 4 | 14.2 | 11.2 |
| 8 | 36.8 | 33.5 |
| 12 | 58.4 | 55.0 |
| 16 | 75.4 | 77.2 |
| 24 | 94.8 | 99 |

The substantial equivalence of the tablets dissolution of the invention with respect to the GITS tablets may be noted in Table 3.

EXAMPLE 5

Composition in tablets suitable for a single daily administration equivalent to 60 mg of nifedipine.

Using the granulate described in the Example 4, tablets have been prepared containing 60 mg of nifedipine.

The results of the dissolution test are reported in Table 4 and compared with the commercial product obtained by the GITS technology of equivalent dosage.

TABLE 4

| Hours | Example 5 Dissolution % | 60 mg GITS tablets Dissolution % |
|---|---|---|
| 1 | 2.8 | 3.7 |
| 4 | 14.4 | 14.0 |
| 8 | 32.5 | 33.6 |
| 12 | 50.8 | 50.9 |
| 16 | 68.5 | 69.3 |
| 24 | 92.8 | 99 |

EXAMPLE 6

Modification of the dissolution profile by the composition variables. A granulate according to the process described in the Example 4 has red decreasing by 25% the hydroxypropylmethylcellulose content and by 50% the carboxypolymethylene one and maintaining constant the other components.

The obtained tablets have the dissolution profile reported in Table 5 in comparison with the dissolution of the Example 4.

TABLE 5

| Hours | Example 6 Dissolution % | Example 4 Dissolution % |
|---|---|---|
| 1 | 11.3 | 2.6 |
| 4 | 26.0 | 14.2 |
| 8 | 48.9 | 36.8 |
| 12 | 68.1 | 58.4 |
| 16 | 87.5 | 75.4 |
| 24 | 98.8 | 94.8 |

EXAMPLE 7

A granulate has been prepared by the same process described in the Example 4 decreasing by 25% the hydroxypropylmethylcellulose content and by 75% the carboxypolymethylene and increasing the lactose content by 50%. The obtained dissolution profile is compared, in Table 6, with the dissolution of the Example 6.

TABLE 6

| Hours | Example 7 Dissolution % | Example 6 Dissolution % |
|---|---|---|
| 1 | 13.8 | 11.3 |
| 4 | 32.1 | 26.0 |
| 8 | 55.5 | 48.9 |
| 12 | 76.5 | 68.1 |
| 16 | 97.8 | 86.5 |
| 24 | — | 98.8 |

The Examples 4, 6 and 7 show that the dissolution profile may be modified with foreseeable results modifying the hydroxypropylmethylcellulose, carboxypolymethylene and lactose content.

EXAMPLE 8

Composition in tablets suitable for 2 daily administrations equivalent to 20 mg of nifedipine.

A composition having a dissolution profile suitable to the administration every 12 hours of 20 mg of nifedipine has been prepared.

The granulate is prepared as described in the Example 2, with the percent composition listed below:

Substances of the tablet
nifedipine 18.02% by weight
polyvinylpyrrolidone 18.02% by weight
microcrystalline cellulose 45.06% by weight
hydroxypropylmethylcellulose 5.41% by weight
carboxypolymethylene 1.60% by weight
magnesium stearate 0.87% by weight
lactose 9.21% by weight
Substances of the coating
talc 0.55% by weight
magnesium stearate 0.28% by weight
titanium dioxide 0.41% by weight
iron oxide 0.05% by weight
methacrylic acid polymer 0.42% by weight
polyethylene glycol 4000 0.09% by weight

TABLE 7

| Hours | Example 8 Dissolution % |
|---|---|
| 1 | 29.3 |
| 4 | 68.4 |
| 8 | 79.9 |

EXAMPLE 9

Composition in capsules suitable for a single daily administration equivalent to 30 mg of nifedipine.

Using a fluidized bed plant, the coprecipitate of nifedipine and polyvinylpyrrolidone 1:1, hydroxypropylmethylcellulose and carboxypolymethylene have been applied on inert cores of saccharose and starch obtaining spheroidal particles (pellets) having a diameter about equal to 1200 micron.

The obtained spheroids have been coated with a solution 1:10 of kind A and kind B methacrylate ammonium copolymers respectively, plasticized with glyceryl triacetate. The process has been carried out in the same fluidized bed plant, with intake of talc as lubricant and antistatic during the process.

Percent composition:
talc 12.18
hydroxypropylmethylcellulose 2.44
polyvinylpyrrolidone 12.18
carboxypolymethylene 0.81
inert cores 45.45
ammonium methacrylate copolymers 21.10
talc 1.62
glyceryl triacetate 4.22

The obtained spheroids have been dosed in capsules of gelatin in order to obtain some dosage units equivalent to 30 mg of nifedipine.

Such capsules have been submitted to the dissolution test. The Table 8 shows the comparison between the composition obtained according to the present Patent and the tablets available on the market produced by the GITS technology and prescribed for a single daily administration equal to 30 mg.

TABLE 8

| Hours | Example 9 Dissolution % | 30 mg/GITS Dissolution % |
|---|---|---|
| 1 | 8.5 | 3.0 |
| 4 | 14.4 | 11.2 |
| 8 | 42.4 | 33.5 |
| 12 | 66.8 | 55.0 |
| 16 | 87.7 | 77.2 |
| 24 | 100.0 | 99 |

EXAMPLE 10

Composition in capsules suitable for a single daily administration of 60 mg of nifedipine.

The pellets obtained as described in the Example 6 have been dosed in gelatin capsules in order to obtain dosage units equivalent to 60 mg of nifedipine.

The Table 9 shows the dissolution test results in comparison with the tablets available on the market produced by the GITS technology, dosed at 60 mg, for single daily administration.

TABLE 9

| Hours | Example 10 Dissolution % | GITS Dissolution % |
|---|---|---|
| 1 | 8.9 | 3.7 |
| 4 | 16.1 | 14.0 |
| 8 | 45.4 | 33.6 |
| 12 | 69.1 | 50.9 |
| 16 | 88.0 | 69.3 |
| 24 | 99.2 | 99.3 |

The reported Examples refer to dosages equal to 20, 30 and 60 mg which represent the dosages more commonly used in therapy for one or two daily administrations. It is clear that the formulations of the previous Examples are also suitable for the scalar dosages and tablets or capsules may be prepared with different dosages such as, for example 10, 20, 30, 40, 60, 80, 90 mg per dose of administration, and also beyond these limits.

For each formulation in microgranules or spheroids administered as they are used to prepare tablets or capsules, from 0.1 to 400 mg of nifedipine may be dosed. Maintaining the percent composition fixed the dissolution profile is reproduced.

I claim:

1. Controlled release pharmaceutical compositions for oral administration containing nifedipine as active substance, in a pharmaceutical dosage form, comprising:

an amorphous coprecipitate of nifedipine and polyvinylpyrrolidone;

a hydrophilic derivative of cellulose in an amount by weight ranging from 0.1 to 6 times with respect to the nifedipine, carboxypolymethylene and lactose in an amount by weight ranging from 0.1 to 5 times with respect to the nifedipine wherein said amounts of the hydrophilic derivative of cellulose, carboxypolymethylene and lactose allow the nifedipine to have a release time between 8 and 24 hours when administered orally.

2. The composition of claim 1 wherein the pharmaceutical dosage form is a tablet.

3. The composition of claim 1 wherein the pharmaceutical dosage form is a capsule.

4. Compositions as claimed in claim 1, wherein the ratio by weight between nifedipine and polyvinylpyrrolidone in said coprecipitate ranges from 1:1 to 1:5.

5. Compositions as claimed in claim 1, wherein the nifedipine content per dosage unit ranges from 0.1 to 400 mg.

6. Compositions as claimed in claim 1, wherein said coprecipitate has a granulometry lower than 100 micrometers.

7. Compositions as claimed in claim 1, wherein said hydrophilic derivative of cellulose is selected from the group consisting of hydroxypropylmethyl cellulose, hydroxyethylcellulose, hydroxymethylcellulose, hydroxypropylcelllulose, carboxymethylcellulose and mixtures thereof.

8. Process for the preparation of pharmaceutical compositions for oral administration which contain nifedipine as the active substance, said process comprising the steps of:

a) preparing an amorphous coprecipitate which comprises nifedipine and polyvinylpyrrolidone by dissolving nifedipine and polyvinylpyrrolidone in methylene chloride and spray drying the solution at a temperature of 90° C.;

b) preparing spheroidal granules comprising said coprecipitate, a hydrophilic derivative of cellulose, carboxypolymethylene, lactose and processing aids by means of a fluidized bed; and c) preparing a pharmaceutical dosage form from the spheroidal granules of step b).

9. The process of claim 8 wherein the pharmaceutical dosage form is a tablet.

10. The process of claim 8 wherein the pharmaceutical dosage form is a capsule.

11. The process as claimed in claim 8 wherein the methylene chloride solution of nifedipine and polyvinylpyrrolidone has a concentration of nifedipine ranging from 2.5 to 20% by weight and a ratio by weight between nifedipine and polyvinylpyrrolidone of from 1:1 to 1:5.

12. Controlled release pharmaceutical compositions for oral administration containing nifedipine as active substance, in a pharmaceutical dosage form, consisting essentially of:

an amorphous coprecipitate which consists essentially of nifedipine and polyvinylpyrrolidone;

a hydrophilic derivative of cellulose in an amount by weight ranging from 0.1 to 6 times with respect to the nifedipine, carboxypolymethylene and lactose in an amount by weight ranging f ro m 0.1 to 5 times with respect to the nifedipine wherein said amounts of the hydrophilic derivative of cellulose, carboxypolymethylene and lactose allow the nifedipine to have a release time between 8 and 24 hours when administered orally.

13. Process for the preparation of pharmaceutical compositions for oral administration which contain nifedipine as the active substance as defined in claim 8, said process comprising the steps of:

a) preparing an amorphous coprecipitate which consists essentially of nifedipine and polyvinylpyrrolidone by weight dissolving nifedipine and polyvinylpyrrolidone in methylene chloride and spray drying the solution at a temperature of 90° C.;

b) preparing spheroidal granules comprising said coprecipitate, a hydrophilic derivative of cellulose, carboxypolymethylene, lactose and processing aids by means of a fluidized bed; and c) preparing a pharmaceutical dosage form from the spheroidal granules of step b).

* * * * *